United States Patent [19]

Verduijn

[11] Patent Number: 5,491,119
[45] Date of Patent: Feb. 13, 1996

[54] ZEOLITE L

[75] Inventor: Johannes P. Verduijn, Spijkenisse, Netherlands

[73] Assignee: Exxon Chemical Patents Inc., Houston, Tex.

[21] Appl. No.: 855,017

[22] PCT Filed: Oct. 30, 1990

[86] PCT No.: PCT/US90/06306

§ 371 Date: Jun. 30, 1992

§ 102(e) Date: Jun. 30, 1992

[87] PCT Pub. No.: WO91/06367

PCT Pub. Date: May 16, 1991

[30] Foreign Application Priority Data

Oct. 30, 1989 [GB] United Kingdom .................. 8924410

[51] Int. Cl.⁶ ............................ B01J 29/30; C01B 33/34; C07C 2/76
[52] U.S. Cl. ............... 502/74; 208/135; 423/716; 502/60; 502/66; 585/407
[58] Field of Search ................... 502/60, 66, 74; 423/328, 716; 585/407

[56] References Cited

U.S. PATENT DOCUMENTS

| | | | |
|---|---|---|---|
| 4,544,539 | 10/1985 | Wortel | 423/328 |
| 4,680,280 | 7/1987 | Pandey et al. | 502/74 |
| 4,894,214 | 1/1990 | Verduijn et al. | 423/328 |
| 5,051,387 | 9/1991 | Koetsier et al. | 502/74 |
| 5,242,675 | 9/1993 | Verduijn | 423/700 |

FOREIGN PATENT DOCUMENTS 219354 4/1987 European Pat. Off. .

*Primary Examiner*—Asok Pal
*Attorney, Agent, or Firm*—Edward F. Sherer

[57] ABSTRACT

Potassium zeolites of type L in which the crystals are very flat cylinders of "hockeypuck" or "coin" shape may be prepared by adjusting the $K_2O/SiO_2$ and $SiO_2/Al_2O_3$ ratio and including in the mixture from which the zeolite is crystallized a small amount of divalent cation such as magnesium or barium. The resulting zeolite has a short channel length and is particularly useful as a base for aromatization catalysis.

30 Claims, 5 Drawing Sheets

ZEOLITE L

FIELD OF THE INVENTION

The present invention relates to a zeolite of the L type, and a process for its production. This zeolite is a good catalyst base for a variety of organic reactions, especially hydrocarbon conversions, and may be regenerated after use.

BACKGROUND OF THE INVENTION

Zeolite L has been known for some time as an adsorbent and in U.S. Pat. No. 3,216,789 is described as an aluminosilicate of the formula:

$$0.9-1.3 M_{2/n}O : Al_2O_3 : 5.2-6.9\ SiO_2 : yH_2O$$

(where M is an exchangeable cation of valency n and y is from 0 to 9) having a characteristic X-ray diffraction pattern.

EP-A-96479 describes a zeolite L which is particularly useful as a catalyst base in hydrocarbon conversions such as aromatization. The zeolite comprises crystallites in the form of cylinders with a mean diameter of at least 0.1 micron, preferably at least 0.5 micron and with an aspect ratio (ratio of cylinder length to diameter) of at least 0.5. The gel from which the zeolite is obtained comprises the following ratios of components: 2.4 to 3.0 moles $K_2O$, 0.6 to 1.3 moles $Al_2O_3$, 8 to 12 moles of $SiO_2$ and 120 to 240 moles $H_2O$. A particularly preferred gel has the following compositions:

$$2.62 K_2O : Al_2O_3 : 10 SiO_2 : 160 H_2O.$$

The potassium form of zeolite L, hereinafter identified as zeolite KL, may also contain caesium, as described in EP-A-323892.

Typically the zeolite is loaded with one or more metals such as platinum, tin, germanium, rhenium or iridium, particularly platinum, to prepare the desired catalyst.

New forms of zeolite KL are sought which are particularly useful as a catalyst base for aromatization and which permit regeneration of spent catalyst. Imperfections in the zeolite crystals and relatively long uni-directional zeolite channels result in poor utilization of Pt, poor maintenance of catalyst activity, and undesirable secondary reactions. To improve the properties of such a zeolite the channel length of the zeolite should be decreased to well below one micron, but at the same time the surface area of the zeolite crystal should be maintained as large as is practicable, and the crystals should be well-formed i.e. without a significant level of crystal imperfections.

These features are present if well-formed zeolite crystals can be made in the form of very flat cylinders. The present invention provides a zeolite whose crystals have the requisite properties; the present invention also provides a process for producing such zeolites.

SUMMARY OF THE INVENTION

Accordingly the present invention provides a zeolite of the KL-type in which the crystals are cylindrical and have an average length of 0.6 microns or less and an average length:diameter ratio of less than 0.5 and have substantially flat basal planes.

It is believed that in such a zeolite the flatness of the basal planes is an indication of the intrinsic quality of the crystals and the shortness of the crystal length makes for less meandering channels.

DESCRIPTION OF PREFERRED EMBODIMENTS

The cylindrical crystal particles are substantially in the form of cylinders of circular cross-section, and preferably substantially in the form of right circular cylinders where the base is normal to the cylinder axis.

The crystals are coin or hockeypuck shaped and have a relatively large diameter and short length. The "length" of a crystal is a measurement of the outer edge of the crystal perpendicular to the basal plane containing the diameter. The length is typically 0.1 to 0.6 preferably 0.1 to 0.3 microns and the diameter is generally 0.3 to 1.5 microns preferably 0.4–1.0 microns. When the length/diameter ratio is 0.2–0.5 the crystal shape is termed herein as "hockeypuck". When the ratio is less than 0.2 the shape is termed herein as "coin".

The crystals thus possess the advantages of a short channel length and of a relatively large diameter which gives increased selectivity and/or yield when it is used as a base for a catalyst. The average length of time over which the catalyst remains active i.e. the run length of the process before the catalyst requires regeneration is longer with the present form of zeolite than with previous zeolites L of larger channel length and crystal size. Another advantage is that crystals of the present invention are easy to recover from the synthesis magma.

The crystals also have microscopically flat basal planes. This is an indication that the crystals are well-formed and have an acceptably low level of crystal imperfections. A measure of flatness is the ratio of height:length, where the height is the longest measurement in the same direction as the length. Thus if the basal plane contains raised steps or terraces the maximum measurement or height of the crystal will be greater than the measurement of the length. If the basal planes are flat the height:length ratio will be 1. The height:length ratio of the crystals should be as close as possible to 1, but a ratio of up to 1.2 may be tolerated.

The zeolites of the invention are preferably aluminosilicates and will be described hereinafter in terms of aluminosilicates, though other elemental substitutions are possible, for example aluminium may be substituted by gallium, boron, iron and similar trivalent elements, and silicon may be substituted by elements such as germanium or phosphorus.

Preferably the zeolite synthesis mixture comprises water, a source of divalent cation, a source of $K_2O$, a source of $SiO_2$ and a source of alumina. The divalent cation may be a cation of nickel, magnesium, calcium, barium, cobalt, manganese, zinc, copper or tin. Magnesium and barium have each been found to be particularly effective when included in the synthesis mixture for the zeolite. Initial results show that cobalt-containing zeolites are comparable with magnesium or barium-containing zeolites.

The proportions of the materials in the synthesis mixture may be adjusted to obtain the necessary crystal morphology. Preferably the synthesis mixture should contain sources which provide a molar ratio of $K_2O/SiO_2$ of 0.20–0.35 more preferably 0.24–0.30.

Preferably the mixture should contain sources which provide a molar ratio of $SiO_2/Al_2O_3$ of 15–160, more preferably 20–40, and a molar ratio of $H_2O/K_2O$ of 45–70, more preferably 50–65.

The ratios are, as is usual with zeolite synthesis mixtures, interdependent. For example, if a high $SiO_2/Al_2O_3$ ratio is used, then a high $K_2O/SiO_2$ ratio should also be used to obtain the necessary alkalinity.

Thus the zeolite is preferably one which is the crystallization product of a mixture comprising q moles of water, a divalent cation, a source of m moles of $K_2O$, a source of n moles of $SiO_2$ and a source of p moles of $Al_2O_3$ where m:n is 0.2 to 0.35 and n:p is 15 to 160 and q:m is 45 to 70. More preferably m:n is 0.24–0.30, n:p is 20–40 and q:m is 50:65.

A typical ratio of the synthesis mixture is e.g. 2.65 $K_2O/0.5$ $Al_2O_3/10$ $SiO_2/160$ $H_2O$, and a suitably quantity of divalent cation.

Increasing the proportion of alumina tends to increase the ratio of length to diameter, and also to increase the tendency for the contaminant, zeolite W, to form. Increasing the proportion of $H_2O$ also has this effect.

Increasing the proportion of $SiO_2$ congruently increases the dimensions of the crystals produced, and also increases the tendency for undesirable amorphous byproducts to form. Increasing the proportion of potassium increases the tendency for the crystals to have rough basal planes, and hence an increase in the height/length ratio.

The inclusion of a divalent cation source in the zeolite synthesis mixture encourages the formation of flat basal planes and small crystals of low l/d ratio, and reduces the formation of crystalline contaminants such as zeolite W and erionite.

The amount of divalent cation which should be present in the synthesis mixture depends on the particular cation. However, in general up to 250 ppm based on the weight of the synthesis gel is used. Barium may be used in an amount up to 250 ppm, but an advantageous effect is seen when much smaller amounts, such as 100 ppm, are used. Magnesium, on the other hand, need only be present in an amount of about 10 ppm to obtain hockeypuck shaped crystals. Although a source of silica, for example, may contain e.g. magnesium as an impurity it has been found that such silica does not produce the same advantageous effect as when the magnesium or other cation is added to the synthesis mixture from a separate source.

The temperature at which the gel is heated to produce the zeolite also affects the morphology of the crystals produced. If the temperature is reduced then there is more nucleation, producing smaller crystals which have small channel lengths and hence are desirable. However, there is also a tendency for the crystals to have rough domed basal planes so that instead of the crystals being flat cylinders they are clam-like in shape. The crystallization temperature should therefore be chosen with a view to obtaining crystals of as small a size as is reasonable whilst maintaining the desired crystal shape. Typical temperatures used to obtain crystals of the desired shape are 150° to 200° C.

Accordingly, the proportions of the synthesis ingredients substances and the crystallization temperature should be adjusted to obtain the necessary dimensions e.g. length, diameter and shape of crystals, and the proportions and amounts specified above and in the examples are given for guidance.

The zeolite of type KL may be prepared by simple adaptation of techniques known in the art for producing zeolites. For example a source of silica and a source of divalent cations may be mixed with an aqueous solution of an alumina source and a $K_2O$ source, to form a gel and this gel heated to form the zeolite crystals. Typically the gel is heated at 150° to 200° C. for a period long enough to form the crystals. This is generally from 60 to 172 hours, typically between 60 and 160, preferably 60 to 150 hours. In general the lower the temperature the longer the time required to reach the same degree of crystallisation with the same synthesis mixture.

The source of silica may be e.g. solid silica or an aqueous solution or colloid of silica such as that sold under the trade name "Ludox" available from E.I. Dupont de Nemours & Co. Colloidal Sols are preferred since they result in less contaminating phases. However other forms such as silicates may be used. The source of divalent cations may be provided in the form of a powder or a solution, e.g. an aqueous solution of an alkaline earth metal hydroxide.

The source of alumina may be an alumina introduced into the synthesis mixture as e.g. $Al_2O_3$. $3H_2O$ previously dissolved in alkali. It is also possible to introduce a source of alumina into the synthesis mixture in the form of aluminium metal dissolved in alkali.

The source of $K_2O$ is preferably introduced into the synthesis mixture as potassium hydroxide.

During the production of zeolite KL, stirring the synthesis mixture during heating increases nucleation and therefore speeds up the formation of crystals and encourages the formation of smaller crystals. However, this has the disadvantage that it also encourages the formation of the undesirable contaminant, zeolite W. Inclusion of a divalent metal cation according to the present invention allows the synthesis mixture to be stirred during crystallization but suppresses the formation of zeolite W.

The aluminosilicate forms of the invention may be hydrated, typically with from 0 to 9 moles of water per mole of $Al_2O_3$. When used as a catalyst base, the zeolite of the invention is preferably first calcined to remove water. In normal preparation from aqueous gels a hydrated form is first prepared and this may be dehydrated by heating.

The product of the process is predominantly a potassium form of the aluminosilicate. By ion exchange of the product in the manner well-known to zeolite chemistry, other cations such as Na or H can be introduced in place of the potassium.

The zeolite may be treated in the same way as conventional zeolites L to improve its mechanical strength e.g. by forming an extrudate.

A catalyst based on the zeolite may be formed by impregnating or "loading" the zeolite with a metal which promotes the desired reaction e.g. aromatization. The metal is preferably platinum or a mixture of platinum and at least one other metal such as tin, germanium, rhenium or iridium. The total amount of metal loaded on the zeolite is typically 0.4 to 0.8 weight % based on the weight of the zeolite, preferably about 0.6 weight %. The loading may be carried out by processes known in the art.

DESCRIPTION OF THE FIGURES

Reference is made in the examples to five figures:

FIGS. 5(A and B) show the benzene yield and selectivity for three catalysts.

EXAMPLES

Figure 1A:
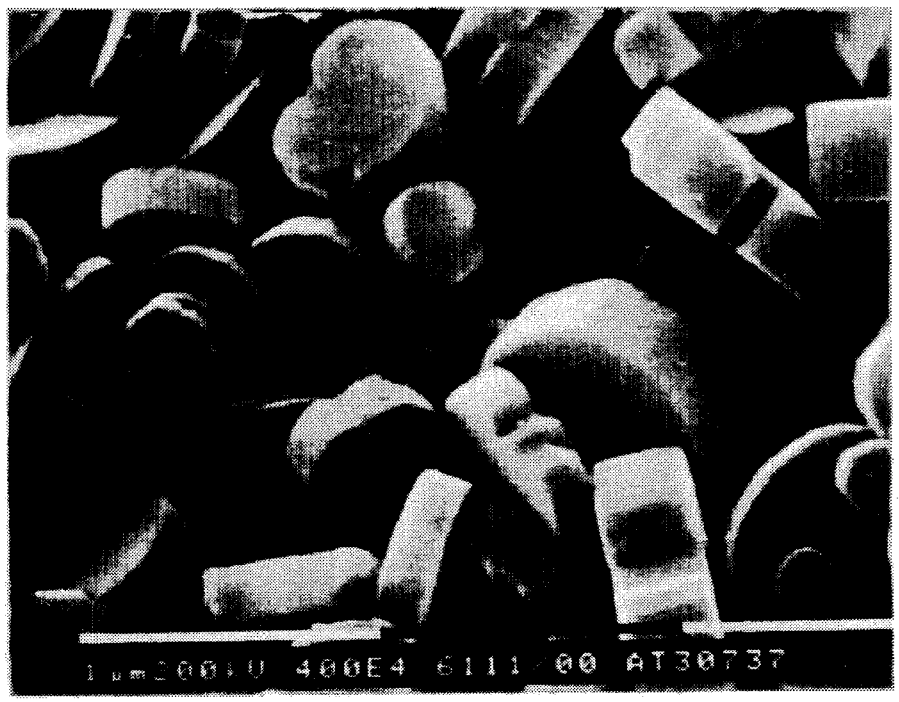
FIGS. 1(A and B) show a scanning electron micrograph (SEM) of "hockeypuck" zeolite crystals.

The following examples illustrate the invention:

EXAMPLE 1

Preparation synthesis mixture (weight of reactants are given in grams).

| POTASSIUM ALUMINATE SOLUTION: | |
| --- | --- |
| KOH pellets (86.8% purity) | 34.30 |
| Al(OH)$_3$, (98.6% purity) | 7.91 |
| H$_2$O | 50.10 |
| Rinse water | 25.00 |
| Silicate Solution: | |
| Collodial Silica (Ludox HS-40*) | 150.26 |
| Ba(OH)$_2$8H$_2$O Crystals | 0.0999 |
| H$_2$O | 50.01 |
| Rinse water | 64.47 |

*Ludox HS-40 is a collodial Silica of DUPONT.

* Ludox HS-40 is a collodial Silica of DUPONT.

The alumina was dissolved in the KOH solution by boiling. The solution was cooled to room temperature and corrected for weight loss.

The Ba-source was dissolved in a portion of the water and was added to the Ludox together with another portion of the water which was used to rinse the beaker containing the Ba-source. The resulting solution was stirred for 5 minutes. Next the aluminate solution including the rinse water was added and the whole was mixed for another 3 minutes.

The composition of the synthesis mixture was: 2.65 K$_2$O/0.0032 BaO/0.5 Al$_2$O$_3$/10 SiO$_2$/159 H$_2$O This corresponds to 115 ppm Ba$^{++}$ based on the weight of the gel. 323.10 g of the synthesis mixture was transferred to a 300 ml stainless steel autoclave. The autoclave was placed in an oven and heated up to 170° C. and was kept at this temperature for 96 hours.

The product was separated from the mother liquor by centrifuging. It was washed to pH 9.7 and dried overnight at 150° C. The weight of the recovered product was 25.1 gram.

The product was analyzed using x-ray diffraction (XRD), Scanning Electron Micrographs (SEM), and Toluene Adsorption Measurement (TGA) with the following results:

XRD: pure KL, crystallinity vs standard: 92%

SEM: flat crystals with microscopically flat basal planes,
  Length: ⁻0.20 microns;
  diameter: ⁻0.60 microns;
  l/d ratio: ⁻0.3;
  height/length (h/l) ratio: 1.

TGA: wt % toluene adsorption at p/po=0.25, T=30° C.:10.6.

EXAMPLE 2: (Comparative)

Synthesis without added divalent cations.

An identical synthesis mixture was prepared as in example 1, but in this case no Ba was added to the synthesis mixture used. The synthesis mixture was crystallized for 96 hours at 170° C. The product was analyzed by XRD and SEM with the following results:

XRD: the product was partially crystalline, e.g. contained amorphous gel particles and was contaminated with an Erionite-like crystalline phase. Crystallinity vs standard: 45%.

SEM: micrographs showed the presence of amorphous gel particles and other contaminants. The KL crystal had a low l/d ratio but the crystals were relatively large and the basal planes showed terraces and step growth. The crystallite dimensions were:

Length: ⁻1.5 microns;
diameter: ⁻4.5 microns;
l/d ratio: ⁻0.3.

From these results can be seen that this experiment did not produce the KL-product of the invention.

EXAMPLE 3

Variation in the source of divalent cation.

An identical synthesis mixture was prepared as in example 1 but in this case the synthesis mixture was seeded with 9 ppm Mg$^{2+}$ (based on the weight of the synthesis mixture). The Mg$^{2+}$ source was Mg(NO$_3$)$_2$. 6H$_2$O. The synthesis mixture was crystallized at 170° C. for 96 hours. The resulting product was analyzed by XRD, SEM and TGA with the following results.

XRD: pure KL, crystallinity vs standard: 97%

SEM: flat KL crystals with microscopically flat basal planes,
  Length: 0.1⁻0.4 microns;
  diameter: 0.4–0.8 microns;
  l/d ratio: ⁻0.4;
  height/length (h/l) ratio: 1.

TGA: wt % toluene adsorption: 10.5.

Examples 4 and 5: variation in the K$_2$O content of the synthesis mixture.

EXAMPLE 4: (Comparative)

This shows the effect of increased K$_2$O level in the synthesis mixture. A synthesis mixture was prepared in the same way as in Example 1 but with a molar composition of:

3.00 K$_2$O/0.0064 BaO/0.50 Al$_2$O$_3$/10 SiO$_2$/160 H$_2$O

This mixture was crystallized for 72 hours at 170° C. The resulting product was analyzed by XRD, SEM and TGA with the following results:

XRD: pure KL, crystallinity vs standard: 76%

SEM: flat KL crystals with terraces on the basal planes,
  Length: ⁻0.15 microns;
  diameter: ⁻0.15–0.3 microns;
  l/d ratio: ⁻0.4;
  height/length (h/l) ratio: >1.

TGA: wt % toluene adsorption: 11.0.

This did not give the crystals of the invention since the basal planes were not sufficiently flat.

EXAMPLE 5

A synthesis mixture was prepared in the same way as in Example 1 but with a molar composition of:

2.40 K$_2$O/0.0064 BaO/0.50 Al$_2$O$_3$/10 SiO$_2$/159 H$_2$O i.e. reducing the alkalinity to the region of its lowest limit.

The mixture was crystallized for 96 hours and for 144 hours at 170° C. The product obtained after 96 hours had a low XRD-crystallinity (53% vs standard) and contained amorphous gel particles. The product after 144 hours crystallization still had a low XRD crystallinity (67% vs standard) and was slightly contaminated with an Erionite-like crystalline phase. The 144 hours—product consisted of flat KL crystals with microscopically flat basal planes. The particle size distribution was significantly increased.

Crystallite dimensions:
  Length: 0.2–0.8 microns
  Diameter: 0.3–1.0 microns
  l/d ratio: 0.2–0.6.

Further examples were carried out in which various parameters were varied in the compositions and their preparations. Table 1 gives details of the synthesis of the various zeolites and Table 2 gives details of the characteristics of the resulting products. Examples 1, 3, 5, 8, 9, 11 to 13 and 15 illustrate the invention.

TABLE 1

SYNTHESIS CHARACTERISTICS

| | | Composition Synthesis Mixture | | | | divalent cations | | Crystallization | |
|---|---|---|---|---|---|---|---|---|---|
| Example | Parameter varied | $K_2O$ | $Al_2O_3$ | $SiO_2$ | $M_2O$ | type | conc wt ppm | time hrs | temp °C. |
| 6 | Reference synthesis | 3.40 | 0.50 | 10 | 160 | — | — | 45 | 150 |
| 2 | Alkalinity, temp, time | 2.65 | 0.50 | 10 | 160 | — | — | 96 | 170 |
| 7 | Time | 2.65 | 0.50 | 10 | 160 | — | — | 144 | 170 |
| 4 | $M^{2+}$ added, alkalinity increased | 3.00 | 0.50 | 10 | 160 | $Ba^{2+}$ | 230 | 72 | 170 |
| 8 | $M^{2+}$ added, alkalinity reduced | 2.65 | 0.50 | 10 | 160 | $Ba^{2+}$ | 230 | 72 | 170 |
| 1 | $M^{2+}$ reduced, time | 2.65 | 0.50 | 10 | 160 | $Ba^{2+}$ | 115 | 96 | 170 |
| 5 | alkalinity reduced | 2.40 | 0.50 | 10 | 160 | $Ba^{2+}$ | 230 | 96 | 170 |
| 5 | time increased | 2.40 | 0.50 | 10 | 160 | $Ba^{2+}$ | 230 | 144 | 170 |
| 3 | variation $M^{2+}$ type | 2.65 | 0.50 | 10 | 160 | $Mg^{2+}$ | 9 | 96 | 170 |
| 9 | $Al_2O_3$ reduced | 3.00 | 0.25 | 10 | 160 | $Ba^{2+}$ | 230 | 72 | 170 |
| 10 | $Al_2O_3$ reduced, no $M^{2+}$ added | 3.14 | 0.176 | 10 | 159 | — | — | 78 | 150 |
| 11 | $M^{2+}$ added | 3.14 | 0.176 | 10 | 159 | $Ba^{2+}$ | 228 | 78 | 150 |
| 12 | $Al_2O_3$ reduced | 3.14 | 0.125 | 10 | 159 | $Ba^{2+}$ | 228 | 118 | 150 |
| 13 | $Al_2O_3$ further reduced | 3.14 | 0.100 | 10 | 159 | $Ba^{2+}$ | 228 | 118 | 150 |
| 14 | $Al_2O_3$ still further reduced | 3.14 | 0.063 | 10 | 159 | $Ba^{2+}$ | 228 | 118 | 150 |
| 15 | Alkalinity adjusted | 3.38 | 0.063 | 10 | 159 | $Ba^{2+}$ | 226 | 118 | 150 |

TABLE 2

PRODUCT CHARACTERISTICS

| | | XRD | | TGA % toluene | SEM Crystallite | | | | | |
|---|---|---|---|---|---|---|---|---|---|---|
| | | % cryst. | | adsorption | L | N | D | l/d | n/l | |
| Example | Parameter varied | (a) | contaminants | (b) | (microns) | | | ratio | ratio | morph.* |
| 6 | Reference synthesis | — | — | — | ~0.1 | ~0.25 | ~0.7 | ~0.15 | 2.5 | fc |
| 2 | Alkalinity, temp, time | 45 | amorphous ERI/OFF | — | ~1.5 | ~2.5 | ~4.5 | ~0.4 | 1.7 | c/l |
| 7 | Time | 72 | ERI/OFF | — | ~1.5 | ~2.5 | ~4.5 | ~0.4 | 1.7 | c/l |
| 4 | $M^{2+}$ added, alkalinity | 76 | none | 11.1 | ~0.15 | spiral steps | ~0.25 | ~0.3 | >1 | hp |
| 8 | $M^{2+}$ added, alkalinity reduced | 89 | none | 10.0 | ~0.15 | ~0.15 | ~0.40 | ~0.4 | 1 | hp |
| 1 | $M^{2+}$ reduced, time | 92 | none | — | ~0.20 | ~0.20 | ~0.60 | ~0.3 | 1 | hp |
| 5 | alkalinity reduced | 53 | amorphous | — | 0.2–0.8 | 0.2–0.8 | 0.3–1.0 | ~0.3 | 1 | hp |
| 5 | time increased | 67 | traces ERI/OFF | — | 0.2–0.8 | 0.2–0.8 | 0.3–1.0 | ~0.3 | 1 | hp |
| 3 | variation $M^{2+}$ type | 97 | none | 10.5 | 0.1–0.4 | 0.1–0.4 | 0.4–0.8 | ~0.4 | 1 | hp |
| 9 | $Al_2O_3$ reduced | 85 | none | 10.8 | 0.1–0.2 | 0.1–0.2 | 0.3–1.0 | ~0.2 | 1 | hp |
| 10 | $Al_2O_3$ reduced, no $M^{2+}$ added | <5 | amorphous | — | — | — | — | — | — | — |
| 11 | $M^{2+}$ added | 74 | none | 1.2 | 0.05–0.1 | 0.05–0.1 | 0.4–0.9 | ~0.1 | 1 | c |
| 12 | $Al_2O_3$ reduced | 77 | none | — | 0.05–0.1 | 0.05–0.1 | 0.6–1.4 | <0.1 | 1 | c |
| 13 | $Al_2O_3$ further reduced | 35 | amorphous | 1.9 | 0.07–0.1 | 0.07–0.1 | 0.8–1.3 | <0.1 | 1 | c |
| 14 | $Al_2O_3$ still further reduced | <5 | amorphous | — | — | — | — | — | — | — |
| 15 | Alkalinity adjusted | 77 | w/l = 0.20 | 8.9 | ~0.1 | ~0.1 | 0.8 | ~0.1 | 1 | c |

(a) = % crystallinity vs. standard

TABLE 2-continued

| | | PRODUCT CHARACTERISTICS | | | | | | |
|---|---|---|---|---|---|---|---|---|
| | | XRD | TGA<br>% toluene | | SEM<br>Crystallite | | | |
| | | % cryst. | adsorption | L | N | D | l/d | n/l |
| Example | Parameter varied | (a) | contaminants | (b) | (microns) | | ratio | ratio | morph.* |

Figure 1B:

(b) = ERI = erionite contaminant
OFF = offretite contaminant
(c) = p/po = 8.25, T = 30° C.
*fc = Flat Clam
c/l = Clam-Like
hp = Hockeypuck
c = Coin FIGS. 1A and 1B show scanning electron micrographs of the crystals of zeolite prepared in Example 1 (using $Ba^{2+}$ as the cation). FIG. 1B shows scanning electron micrographs of crystals of zeolite prepared in Example 3 (using $Mg^{2+}$ as the cation) respectively. The magnification of FIGS. 1A and 1B is 40000 times.

Figure 2A:
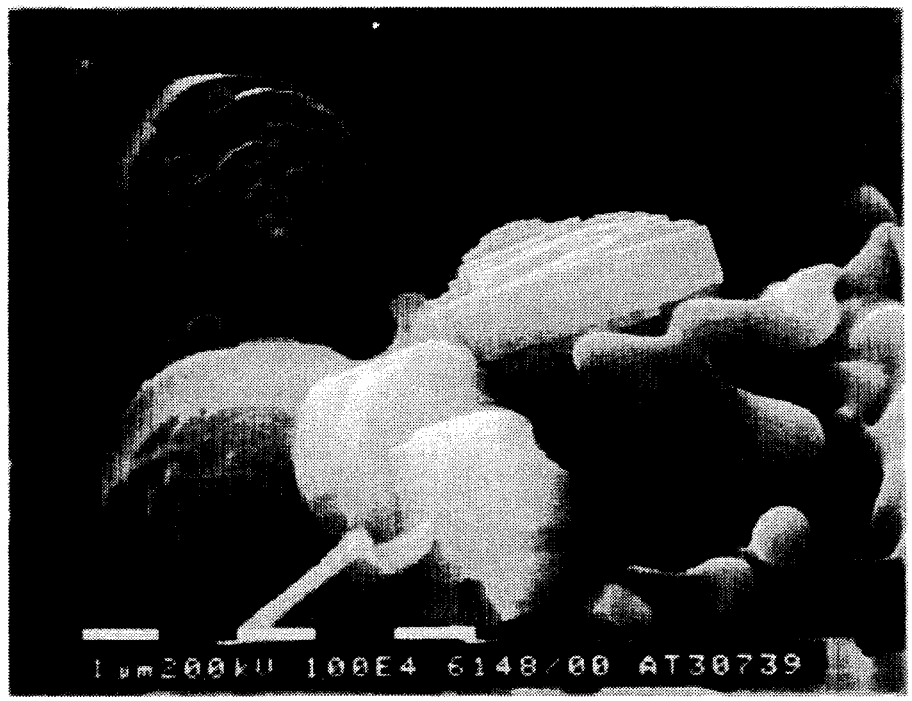
FIGS. 2(A and B) show a SEM of comparative zeolite crystals which are not of the desired shape.
Figure 2B:
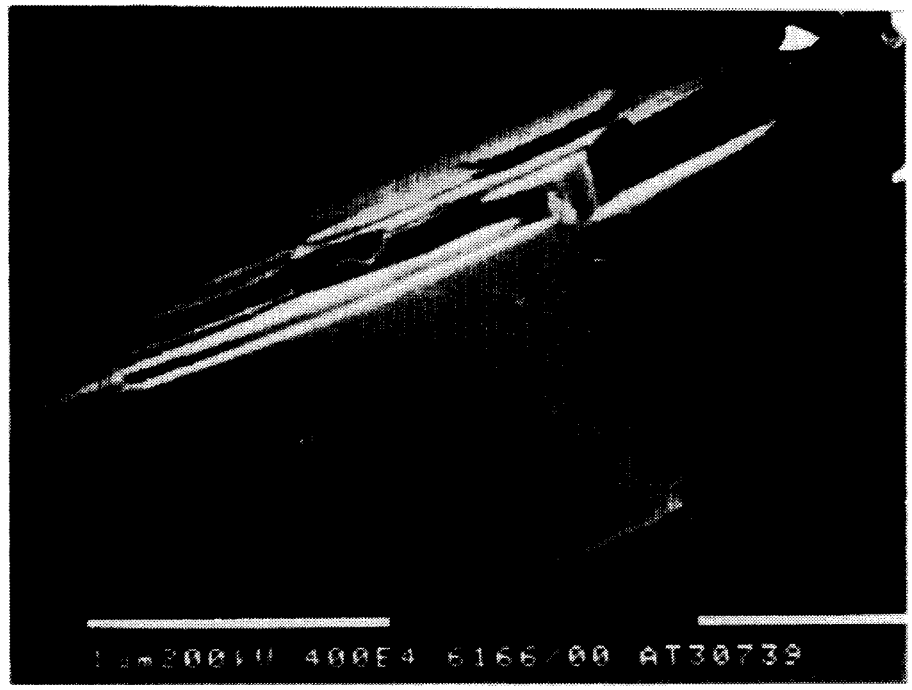

FIGS. 2A and 1B scanning electron micrographs of the crystals of zeolite prepared in Example 2 in which no divalent cation was used. The magnification of FIG. 2A is 10000 times. The magnification of FIG. 2B is 40000 times. A comparison of FIGS. 2A and 2B with FIGS. 1A and 1B shows that the crystals of Example 2 are much larger and do not have flat basal planes.

The wavy lines in the right half of FIGS. 2A and 2B show the contamination by amorphous particles of unreacted gel.

Figure 3A:
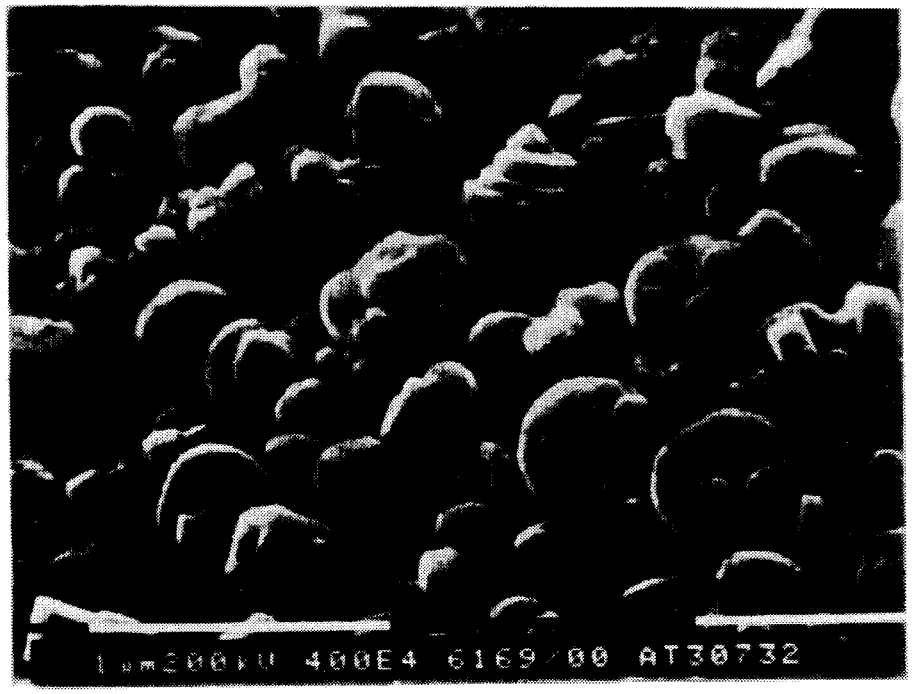
FIGS. 3(A and B) show SEMs of "hockeypuck" zeolite crystals.
Figure 3B:
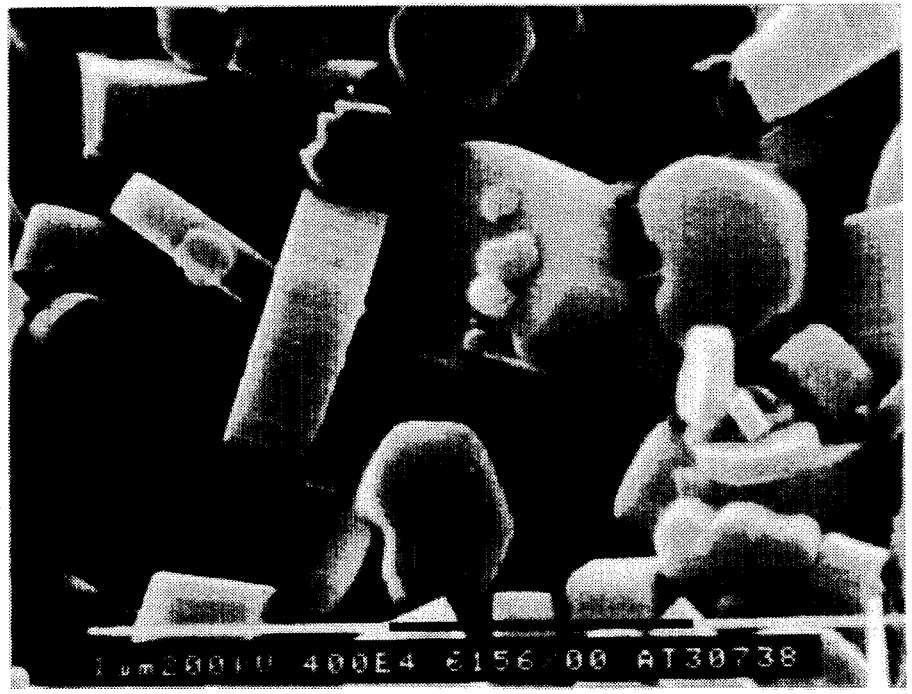

FIGS. 3A and 3B show scanning electron micrographs of the crystals of zeolite prepared in Example 4. FIG. 3B shows scanning electron micrographs of the crystal of zeolite prepared in Example 5 respectively. It can be seen that the crystals of Example 4, in which the K2O content is increased, are not flat and have terraces on the basal planes. The magnification of FIGS. 3A and 3B is 40000 times.

EXAMPLE 16:

This example illustrates the use of $Mg^{2+}$ as the divalent cation, and demonstrates that the slower heating up of a gel which would be a feature of large scale production can be used successfully to produce crystals of the desired shape and dimensions.

25 liters synthesis. Preparation synthesis mixture (weight of reactants given in grams):

| (A) | KOH (87.7% purity) | 1878.06 |
|---|---|---|
| | Al(OH)$_3$ (99.3% purity) | 433.07 |
| | H$_2$O | 3154 ± 5 |
| | Rinse Water | 420.0 |
| (B) | Ludox HS-40 | 8250 ± 5 |
| | Mg(NO$_3$)$_2$6H$_2$O | 2.0484 |
| | H$_2$O | 1799.67 |
| | H$_2$O | 4640 ± 5 |
| | Rinse Water | 420.0 |

SOLUTION A:

The ingredients were dissolved with boiling water under reflux in a 6 liter pyrex bottle and the solution cooled to room temperature.

SOLUTION B:

The $Mg^{2+}$ source was dissolved in 1799.67 grams of the water. In a separate 25 liter polypropylene flask the Ludox was diluted with 4640 grams of water and this solution was poured into the autoclave. The polypropylene flask was rinsed with 420 grams of water and the rinse water added to the autoclave. The $Mg^{2+}$ solution was then poured into the diluted Ludox solution in the autoclave and the whole was mixed for 5 minutes.

Solution A was then added and mixing was continued for a further five minutes. A thick, smooth gel was obtained.

The gel composition was:

2.67 K$_2$O/0.50 Al$_2$O$_3$/10 SiO$_2$/160 H$_2$O+9 ppm $Mg^{2+}$

The gel was heated up over 10 hours to 170° C. although it took approximately 13 hours for the centre of the autoclave to reach 170° C. The autoclave was maintained at 170° C. for 93 hours.

Before heating the gel a small sample (123.77 grams) of the gel was removed and crystallized separately as a satellite batch in an oven.

After crystallization a sample was taken from the main batch, washed to pH10.2 and the product was dried for 6 hours at 126° C. and 16 hours at 150° C. The weight of product recovered was 200 grams.

Samples from the main and satellite batches were analysed. X-ray diffraction showed the crystallization of the main batch to be 95% compared with the standard, and the crystallization of the satellite sample to be 96% compared to the standard.

Both products were very slightly contaminated with erionite.

Figure 4A:
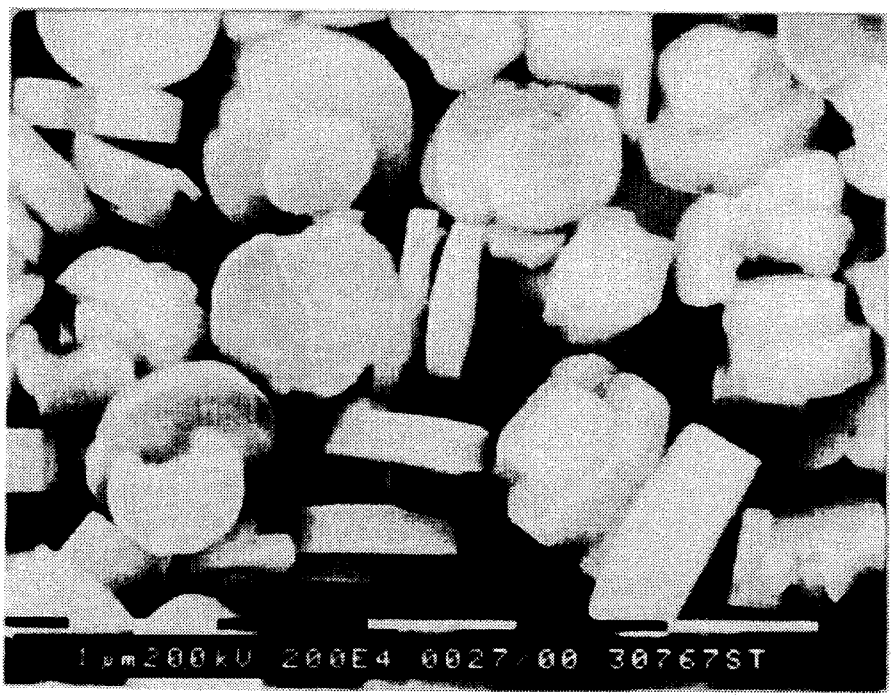
FIGS. 4(A, B, C, and D) shows SEMs of "hockeypuck" zeolite crystals made in a large volume and a small volume synthesis.
Figure 4B:
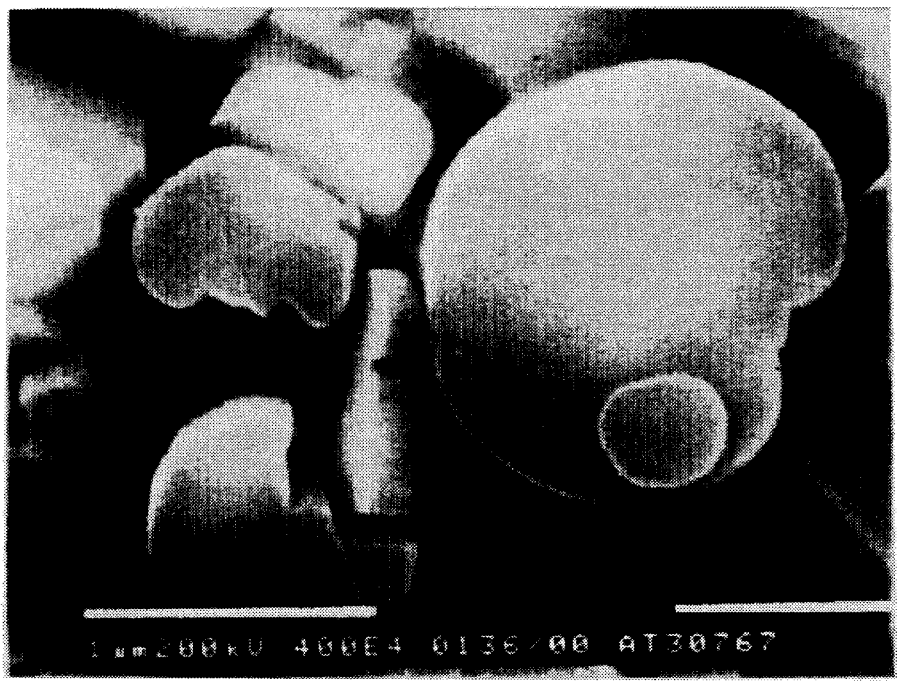
Figure 4C:
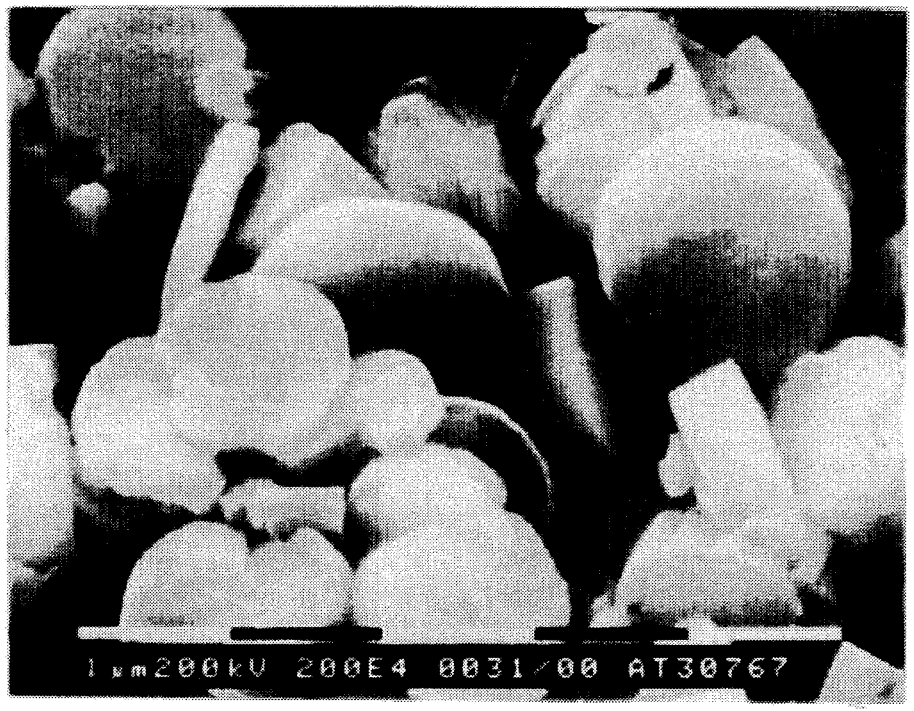
Figure 4D:

FIGS. 4(A), 4(B), 4(C) and 4(D) show the scanning electron micrographs of the crystals of zeolite prepared according to this example. FIGS. 4A and 4B are the satellite batch. FIGS. 4C and 4D are the batch crystallized in the 25 liter autoclave. FIGS. 4A and 4C are at magnification 20000 times, and FIGS. 4B and 4D are at magnification 40000. It can be seen that both batches give hockeypuck shaped crystals with flat basal planes.

EXAMPLE 17

The effectiveness of the zeolite KL of the present invention as a base for an aromatization catalyst was compared with that of a reference zeolite KL which was a zeolite KL prepared according to EP-A-96479. Using similar techniques to the previous examples the following zeolites were prepared, and loaded according to known techniques with nominally 0.6 wt % Pt.

| ZEOLITE | ZEOLITE TYPE | LENGTH (microns) | DIAMETER (microns) |
|---|---|---|---|
| Reference | Standard KL Type | 0.8–1.3 | 1.1–1.3 |
| Example 8 | Ba added. Hockeypuck crystals with flat basal planes | 0.1–0.2 | 0.4–0.6 |
| Example 16 | Mg added Hockeypuck crystals with flat basal planes | 0.2–0.6 | 0.6–1.5 |

A feedstock of 54% 3-methylpentane, 36% n-hexane, and 10% methylcyclopentane was subjected in the presence of each of the above zeolite catalysts to a temperature of 510° C. and 135 psig (930 kPa) total pressure for 170 hours. The $H_2$/Feed ratio was 4.

FIG. 5(A) shows the benzene yield (FIG. 5A) versus time for the three catalysts and FIG. 5(B) shows benzene selectivity vs. time for the three catalysts. It can be seen that the very flat cylindrical (hockeypuck) crystals give a better yield and selectivity. Regression analysis performed on the data obtained gave the following results:

TIME AVERAGE VALUE (92 HOURS)

| CATALYST | YIELD | SELECT-IVITY | CON-VERSION | CYCLE LENGTH (hr) at 38% TAY |
|---|---|---|---|---|
| REFERENCE | 52.2 | 58.9 | 88.0 | 2056 |
| EXAMPLE 8 | 60.2 | 64.3 | 93.0 | 7982 |

TAY is the Time Average Yield. This is a measure of the time over which the catalyst produces a benzene yield of at least 38%. The higher the TAY the longer the catalyst functions before it needs to be regenerated.

It can be seen that the improved stability of the "hockeypuck" catalyst gives a greater selectivity and yield and also allows for a greatly increased cycle length compared with the reference catalyst of KL type.

I claim:

1. A Crystalline type L Zeolite L in which the crystals are cylindrical and have an average length of 0.6 microns or less and an average length:diameter ratio of less than 0.2 and have substantially flat basal planes.

2. A zeolite as claimed in claim 1 in which the average height:length ratio of the crystals is 1 to 1.2.

3. A zeolite as claimed in claim 2 in which the average height:length is approximately 1.

4. A catalyst comprising a zeolite as claimed in claim 1 which is impregnated with an aromatization promoter metal.

5. A catalyst as claimed in claim 4 in which the metal is selected from the group comprising platinum and platinum mixed with at least one other metal.

6. A catalyst as claimed in claim 5 in which the other metal mixed with platinum is selected from the group comprising tin, germanium, iridium and rhenium.

7. A catalyst as claimed in claim 6 in which the promoter metal is present in an amount of 0.4 to 0.8 weight % based on the weight of the zeolite.

8. A zeolite as claimed in claim 1 wherein the length of said crystals is in the range of from 0.1 to 0.3 microns.

9. A zeolite as claimed in claim 1 wherein the diameter of said crystals in the range of from 0.3 to 1.5 microns.

10. A zeolite as claimed in claim 9 wherein said diameter is in the range of from 0.4 to 1.0 microns.

11. A process for preparing a crystalline aluminosilicate L zeolite in which the crystals are cylindrical and have an average length of 0.6 microns or less and an average length: diameter ratio of less than 0.2 comprising:

a. forming a mixture of q moles of water, a divalent cation, a source of m moles of $K_2O$, a source of n moles of $SiO_2$ and a source of p moles of $Al_2O_3$ wherein m:n is 0.2 to 0.35, n:p is 15 to 160 and q:m is 45 to 70; and b. heating said mixture for a period of time sufficient to crystallize the zeolite.

12. A process as claimed in claim 11 where m:n is 0.24 to 0.30 and n:p is 20 to 40 and q:m is 50 to 65.

13. A process as claimed in claim 12 in which the divalent cation is nickel, magnesium, calcium, barium, cobalt, manganese, zinc, copper or tin.

14. A process as claimed in claim 13 in which the cation is magnesium or barium.

15. A process as claimed in claim 14 in which the cation is magnesium.

16. A process according to claim 11 in which the mixture is heated to 150° to 200° C.

17. A process according to claim 16 in which the mixture is heated for 60 to 160 hours.

18. A process as claimed in claim 11 wherein said divalent cation is present in said mixture at a level of up to 250 ppm.

19. A process as claimed in claim 11 wherein m:n is 0.24 to 0.30, n:p is 20 to 40 and q:m is 50 to 65.

20. A process for the aromatization of a petroleum hydrocarbon feed stream comprising contacting the feed stream under aromatization conditions with a crystalline KL zeolite impregnated with an aromatization promoter metal, in which the crystals of said zeolite are cylindrical and have an average length of 0.6 microns or less and an average length:diameter ratio of less than 0.2 and have substantially flat basal planes.

21. A process as claimed in claim 20 in which the promoter metal is selected from the group comprising platinum and platinum mixed with at least one other metal.

22. A process as claimed in claim 21 in which the other metal mixed with platinum is selected from the group comprising tin, germanium, iridium and rhenium.

23. A process as claimed in claim 20 in which the promoter metal is present in an amount of 0.4 to 0.8 weight % based on the weight of the zeolite.

24. A process as claimed in claim 20 in which the average height:length ratio crystals is 1 to 1.2.

25. A process as claimed in claim 24 in which the average height:length of said crystals is approximately 1.

26. A process as claimed in claim 20 wherein the length of said crystals is in the range of from 0.1 to 0.3 microns.

27. A process as claimed in claim 20 wherein the diameter of said crystals in the range of from 0.3 to 1.5 microns.

28. A process as claimed in claim 27 wherein said diameter is in the range of from 0.4 to 1.0 microns.

29. A process as claimed in claim 20 wherein said KL zeolite is prepared from a synthesis mixture containing q moles of water, a divalent cation, a source of m moles of $K_2O$, a source of n moles of $SiO_2$, and a source of p moles of $Al_2O_3$ wherein m:n is 0.2 to 0.35, n:p is 15 to 160 and q:m is 45 to 70.

30. A process as claimed in claim 29 wherein m:n is 0.24 to 0.30, n:p is 20 to 40 and q:m is 50 to 65.

* * * * *